United States Patent [19]

Gobran

[11] Patent Number: 5,453,319
[45] Date of Patent: Sep. 26, 1995

[54] HOT-MELT-COATABLE ADHESIVES

[75] Inventor: Ramsis Gobran, Roseville, Minn.

[73] Assignee: Minnesota Mining and Manufacturing Company, St. Paul, Minn.

[21] Appl. No.: 249,732

[22] Filed: May 26, 1994

Related U.S. Application Data

[62] Division of Ser. No. 885,283, May 18, 1992, Pat. No.5,342,685.

[51] Int. Cl.$^6$ .................................. B32B 7/12; C08L 9/00
[52] U.S. Cl. .......................... 428/355; 525/98; 525/99; 525/314
[58] Field of Search ....................... 428/343, 355; 525/98, 99, 314

[56] References Cited

U.S. PATENT DOCUMENTS

| | | | |
|---|---|---|---|
| 3,519,585 | 7/1970 | Miller | 260/27 |
| 3,592,710 | 7/1971 | Yurgen et al. | 156/153 |
| 3,787,531 | 1/1974 | Dahlquist et al. | 260/876 B |
| 3,932,328 | 1/1976 | Korpman | 428/355 |
| 4,080,348 | 3/1978 | Korpman | 525/98 |
| 4,096,203 | 6/1978 | St. Clair | 260/876 B |
| 4,104,327 | 8/1978 | Inoue et al. | 260/876 B |
| 4,131,709 | 12/1978 | Schunck et al. | 525/98 |
| 4,136,071 | 1/1979 | Korpman | 525/98 |
| 4,652,491 | 3/1987 | Gobran | 428/355 |
| 4,717,749 | 1/1988 | Tang et al. | 524/505 |
| 4,944,993 | 7/1990 | Raykovitz et al. | 428/290 |
| 5,342,685 | 8/1994 | Gobran | 428/355 |
| 5,352,743 | 10/1994 | Coolbaugh et al. | 525/314 |

FOREIGN PATENT DOCUMENTS

| | | |
|---|---|---|
| 63-189485 | 8/1988 | Japan . |
| 1342528 | 6/1971 | United Kingdom ............ C08D/9/02 |
| 89/08128 | 9/1989 | WIPO . |
| 91/13935 | 9/1991 | WIPO . |

OTHER PUBLICATIONS

Kraton Polymers for Adhesives and Sealants, Shell Chemical Company, Formulating Adhesives based on Kraton Polymers.

*Primary Examiner*—George F. Lesmes
*Assistant Examiner*—Blaine R. Copenheaver
*Attorney, Agent, or Firm*—Gary L. Griswold; Walter N. Kim; William J. Bond

[57] ABSTRACT

A hot melt coatable pressure-sensitive adhesive is provided showing high levels of adhesion to low surface energy films and nonwovens. The adhesive elastomeric phase comprises from 78 to 98 parts by weight of a diblock A–B type block copolymer with an elastomeric block of 1,3-polybutadiene with 2 to 22 parts by weight of multiblock A–B type block copolymer. The tackifying material comprises 140 parts or less of a solid tackifying resin and a liquid tackifier to provide an adhesive having a composite midblock glass transition temperature of less than −10° C.

16 Claims, 1 Drawing Sheet

HOT-MELT-COATABLE ADHESIVES

This is a division of application Ser. No. 07/885,283 filed May 18, 1992, now U.S. Pat. No. 5,342,685.

BACKGROUND AND FIELD OF THE INVENTION

This invention relates to an improved hot-melt-coatable pressure-sensitive adhesive for use in adhering to low surface energy substrates and nonwovens. More specifically, the invention relates to a pressure-sensitive adhesive composition which provides superior adhesion characteristics when used against a polyethylene film or a nonwoven such as are used in typical diaper constructions.

U.S. Pat. No. 3,787,531 (Dahlquist) relates to a tacky pressure-sensitive adhesive described as having excellent shear strength and creep resistance at elevated temperatures. Dahlquist teaches that the use of tapered diblock elastomers produce adhesives that are useless for commercial pressure-sensitive adhesive tapes due to their tendencies to fail cohesively, specifically mentioning styrene-butadiene copolymers such as Solprene™ 1205, a tapered diblock copolymer. As a method of improving adhesive performance, Dahlquist proposes the use of pure diblock copolymers where there is no intermingling of monomers from one block in the block of the other, such as in a tapered block copolymer. The exemplified adhesives are comprised predominately of an A–B diblock copolymers of polyisoprene or polybutadiene elastomeric blocks tackified with solid tackifying resins, such as Piccolyte S-115 for the polyisoprene-based diblock adhesives and an alpha polyterpene tackifier for the polybutadiene-based diblock adhesives. The polymers obtained are described as having excellent adhesive properties, particularly high shear strength without the necessity of chemical cross-linking, however, these properties were determined against a conventional stainless steel substrate.

Other patents dealing with pressure-sensitive adhesives using A–B diblock copolymers with butadiene elastomeric blocks, particularly Solprene™ 1205, include U.S. Pat. No. 3,519,585 which describes an adhesive composition comprising 50–95 parts solid wood rosin, 50–95 parts of a styrene-butadiene diblock copolymer with correspondingly 10–50 parts of a styrene-butadiene triblock copolymer. When triblock was used alone, adhesives allegedly demonstrate poor tack strength, but had good shear strength. U.S. Pat. No. 3,592,710 describes an extrudable hot-melt adhesive composition comprised of an admixture of Solprene™ 1205, Kraton™ 1101 and a solid resin Pentalyn™ H. The exemplified adhesive comprises 70 parts Solprene™ 1205, 30 parks Kraton™ 1101 and 85 parts Pentalyn™ H. The adhesive allegedly displays good adhesion properties, while being extrudable. U.K. Patent No. 1,342,528 describes an adhesive composition based on Solprene™ 1205 and a triblock copolymer, cariflex™ 1101, both styrene-butadiene block copolymers. The Solprene™ 1205 is allegedly used in amounts up to 45 parts of the elastomer phase, the elastomer phase being tackified with a solid tackifier and an oil or liquid tackifier. It is alleged that the liquid tackifying agent surprisingly improves the surface tack or wet-grab properties of the adhesive without compromising shear resistance. The application only contemplates the use of the Solprene™ 1205 diblock copolymer in amounts up to 45 parts per 100 parts of the elastomeric phase, with Example 4 indicating that, at this level, tack significantly decreases.

U.S. Pat. No. 4,096,203 describes a method to obtain high tack adhesives which fail cohesively by varying the coupling efficiency of the elastomer. The elastomer comprises up to 80% A–B diblock copolymer.

The examples demonstrate coupling efficiency, at the low end, of 0 and 25% of styrene-isoprene/styrene-isoprene-styrene block copolymer systems tackified with $C_5$ aliphatic hydrocarbon resin, alone and with an oil. Both systems failed cohesively, however the 0% coupled (100% diblock) system had significantly lower peel values and holding power.

U.S. Pat. No. 4,104,327 describes an adhesive prepared with pure triblock styrene-butadiene copolymer tackified with a solid tackifying resin and preferably an oil. It is alleged that the specific tackifying resin employed provides pressure-sensitive adhesives with superior properties versus compositions tackified with conventional terpene resins or aliphatic hydrocarbon resins, which are stated as having inferior tack, adhesive strength and cohesive force.

U.S. Pat. No. 4,944,993 discloses a hot-melt adhesive based on a radial styrene-butadiene copolymer with a solid tackifying resin and, optionally, an oil. The adhesive described is allegedly useful as a hot-melt construction adhesive, not a pressure-sensitive adhesive, for disposable articles such as sanitary napkins, hospital gowns, hospital bed pads, and the like. Specifically, it is stated that the adhesives show superior abilities to be used in spray fiberization techniques used in the construction of such disposable products. None of the above patents address the difficulties in adhering to low surface energy substrates or nonwovens, which problems are addressed by the present invention.

BRIEF SUMMARY OF THE INVENTION

There is provided a pressure-sensitive adhesive comprising 100 parts of an elastomeric phase having 78–98 parts of an elastomeric diblock A–B type block copolymer of predominately polystyrene or derivatives A blocks, and poly-1,3-butadiene B blocks. The elastomeric phase is tackified with an admixture of a solid tackifying resin and an oil or liquid tackifier to provide an adhesive having a composite midblock glass transition temperature (CMTg) of less than $-10°$ C. The resulting pressure-sensitive adhesive securely adheres to low surface energy and discontinuous surfaces such as polyethylene films and nonwovens, respectively.

DETAILED DESCRIPTION OF THE INVENTION

Figure 1:
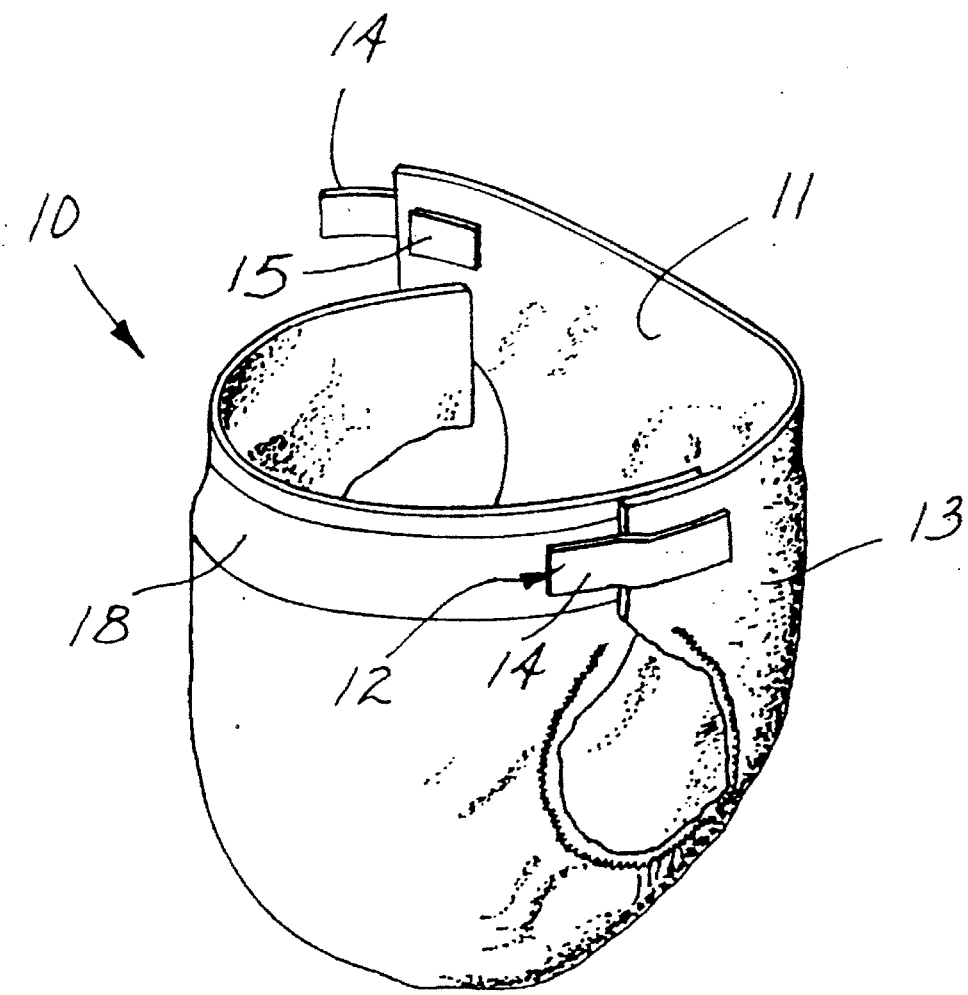
FIG. 1 is a diaper using adhesive tapes of the invention.

The invention adhesive comprises an elastomeric phase which is comprised predominately of diblock A–B type block copolymers wherein the A blocks are of a monoalkenyl aromatic hydrocarbon or a monoalkenyl arene, mainly polystyrene or polystyrene derivatives, having a molecular weight between 4,000 and 50,000, preferably between 7,000 and 30,000, and the B blocks are comprised predominately of 1,3-butadiene. The A block content is from about 7–50 weight percent of the block copolymer, preferably 10–35 weight percent. The A block can also be formed predominately of alphamethylstyrene, t-butylstyrene, and other ring alkylated styrenes and may also contain minor proportions of other monomers, such as conjugated dienes. The B groups have an average molecular weight of from about 5,000 to 500,000, preferably from about 50,000 to 300,000. Minor proportions of other monomers may be included in the B blocks, e.g., residue arenes or other conjugated dienes. B groups may also contain conjugated dienes other than 1,3-butadiene in amounts up to 50 percent by weight of the total B blocks. Other A–B type block copolymer elastomers or other conventional elastomers, preferably diene elastomers, may be employed in amounts up to 75 percent of the multiblock portion of the elastomeric phase, however, preferably, less than 50 percent of the multiblock portion of the elastomeric phase of the adhesive.

The remaining portion of the elastomeric phase comprises multiblock A–B, linear (other than diblock), star, radial or otherwise branched, type block copolymer of the above-described A blocks, and B blocks of conjugated dienee, preferably, 1,3-butadiene. This multiblock A–B type block copolymer has three or more blocks, the terminal portion of at least two branches or ends are preferably of A blocks. Preferably, this portion of the elastomeric phase comprises a linear triblock A–B type block copolymer.

The diblock portion of the elastomeric phase preferably comprises from 78–98 parts, more preferably, from 80–95 parts of the elastomeric phase. At diblock amounts greater than 98 parts, the resulting adhesives lose substantially all shear strength, while below 78 parts, the peel adhesion becomes unacceptable. Preferably, the diblock A–B type block copolymer is used in amounts of less than 95 parts of the 100 parts elastomeric phase to retain the high cohesive strength of the adhesive.

The diblock copolymer can be formed by conventional block copolymer polymerization techniques involving the use of organic alkali metal initiators such as sec-butyl lithium. The polymerization can proceed sequentially with the step-wise addition of monomers, or simultaneously, with mixtures of monomers having substantially differing rates of reaction, producing tapered block copolymers such as Solprene™ 1205. Multiblock copolymers can also be formed by the use of conventional coupling agents used to join living polymer chains which allows wider variation in molecular weight at much shorter reaction times than with the sequential addition of reactants.

The invention adhesive composition further comprises a tackifying material comprising a blend of solid tackifying resin and liquid tackifying resin, or a blend of solid tackifying resin and liquid plasticizer and/or liquid tackifying resin. The solid tackifying resin and liquid tackifying resin or plasticizing oil are provided in amounts such as to provide an adhesive having a composite midblock glass transition temperature (CMTg) of less than −10° C., preferably greater than −25° C. Solid resin will typically be used at 140 parts or less, preferably from 80 to 135 parts per 100 parts of the elastomeric phase with 5 to 35 parts, more preferably 5 to 30 parts, of oil or liquid tackifying resin.

The solid or liquid tackifying resins are preferably selected from the group of resins at least partially compatible with the 1,3-butadiene blocks of the elastomeric phase. Such tackifying resins include hydrocarbon resins; rosin esters and rosin acids; mixed aliphatic/aromatic tackifying resins; polyterpene tackifying resins; terpene/aromatic tackifying resins; and hydrogenated tackifying resins. The hydrogenated resins can include resins made from the polymerization and subsequent hydrogenation of a feedstock consisting mostly of dicyclopentadiene; resins produced from the polymerization and subsequent hydrogenation of pure aromatic feedstocks such as styrene, alphamethylstyrene, vinyl toluene; resins fashioned from the polymerization and subsequent hydrogenation of an unsaturated aromatic feedstream wherein the feedstream mainly contains species having from 7 to 10 carbon atoms; hydrogenated polyterpene resins; and hydrogenated aliphatic and aliphatic/aromatic resins and rosin esters. Preferred tackifying resins include the polyterpene resins, terpene/aromatic resins and the hydrogenated resins. Especially preferred are the polyterpene resins, such as polyalphapinene, rosin esters or hydrogenated rosin esters.

The liquid plasticizers suitable for use in the adhesive compositions of this invention include naphthenic oils and paraffinic oils. The liquid plasticizers are generally preferred as they have been found to provide better peel adhesion properties, to nonwoven and low surface energy substrates, than liquid tackifiers in the invention adhesive.

Preferably, the solid tackifying resin used is one that is compatible with the elastomeric conjugated diene B block and is preferably a tackifying resin having a softening point between about 80° C. and 135° C.

The CMTg can be calculated using the Fox Equation from measuring the Tg of the midblock of the elastomeric block copolymer and the measured Tg of each tackifying resin and liquid plasticizer oil. The Tg for each component is measured using a differential scanning calorimeter such as a DSC-7, manufactured by Perkin-Elmer. The Tg is measured on the second heating run using a scan rate of 20 degrees Centigrade per minute. The first heating run is made up to well above the softening point of the test material. The sample is subsequently quenched to well below the Tg of the material. Antioxidants added to the adhesive are not figured into the calculation of the CMTg. The Fox Equation is:

$$\frac{\Sigma_i W_i}{CMTg} = \Sigma_i \frac{W_i}{Tg_i}$$

where $W_i$ is the weight fraction of component i and $Tg_i$ is the glass transition temperature of component i. Only the midblock portion of the block copolymer is included in the calculation of the CMTg. For a styrene/butadiene block copolymer, the midblock is the polybutadiene portion of the molecule.

The adhesive composition can also contain conventional additives such as pigments, fillers, stabilizers, and antioxidants for the conventional purposes of these additives.

The above-described pressure-sensitive adhesive finds particular use on tapes designed to adhere to low surface energy polymers or discontinuous, e.g., nonwoven, materials. The tape backing can be of any conventional substrate including polyolefin films, calendered papers, and the like.

The tape finds particular use in diaper or other incontinent article constructions where there is an outer film of a low surface energy material, such as polyethylene or polyethylene blends or copolymers, and an inner liquid-permeable facing of a nonwoven material such as a spun-bond nonwoven where the fibers are occasionally surface treated with a surfactant. Certain components are conventionally permanently adhered to these surfaces using pressure-sensitive adhesive tapes provided in a roll form. Two common tapes adhered to these surfaces include a release tape, for the diaper fastening tab, applied to the diaper nonwoven material, and a frontal reinforcement tape, provided in the parent's bond region, to which the free end of the fastening tab is adhered. Frontal reinforcement tape is generally adhered to the inside or outside face of the polyethylene backsheet material. The invention adhesive provides tapes which firmly and securely bond to these diaper surfaces at high levels of peel and shear adhesion. Although found not necessary, shear adhesion can be increased by electron beam treating the adhesive.

In FIG. 1, there is shown a typical diaper construction 10 having a diaper backsheet of a thin outer plastic film 13 of a low surface energy material such as polyethylene. The inner sheet of the diaper is formed of a liquid-permeable material 11, typically a fibrous nonwoven material. Fastening tab 12 has a free end 14 that is releasably secured to a release tape, the release tape using the invention adhesive to attach to the liquid permeable nonwoven material 11. The free end 14 of the adhesive fastening tab 12 is then adhered to a fastening area 18 to fit the diaper on the wearer. The fastening area can be formed by securing an invention adhesive tape, as a frontal reinforcement tape, to either the inside surface or outside surface of the outer plastic film 13.

Tapes prepared in accordance with the invention were tested as outlined below.

135 degree peel adhesion from partially secured nonwoven

Test panels consisted of 2 inch×5 inch (5.1×12.7 cm$^2$) clean steel panels with a strip of ¾ inch (1.9 cm) double-sided adhesive affixed along each 2 inch (5.1 cm) edge. A sheet of nonwoven was laid down loosely over the test panel so that it laid flat without any wrinkles. The cross direction of the nonwoven was parallel to the long dimension of the test panel. The nonwoven was rolled down firmly onto the ¾ inch (1.9 cm) double-sided adhesive, and any excess which extended beyond the edge of the test panel was trimmed away.

A strip of test tape–1 inch×2.5 inch (2.5 cm×6.4 cm)–with a paper leader measuring 1 inch×8 inch (2.5 cm×20.3 cm), adhered to the final ¼ inch (0.6 cm) of the tape, was laid on the nonwoven. The tape's long dimension was parallel to the long direction of the panel so that it was equidistant from each end of the panel. No additional pressure was exerted in laying down the tape.

The tape was immediately rolled down at 12 inch/minute (30.5 cm/minute) with a single pass in each direction with a 4.5 lb. (2000 gm) rubber roller and was tested within 15 seconds.

The panel was placed in a 135 degree jig. The jig was placed into the bottom Jaw of an Instron™ 1122 while the paper leader was held by the upper jaw. The upper Jaw was set in motion at 30.5 cm/min while the steel panel was moved to keep the peel face in the same position relative to the fixture throughout the peel, and the peel continued until the tape was pulled free of the nonwoven or until the crosshead had traveled 2–½ inches (6.4 cm).

The average peel is reported in N/m.

Shear adhesion

The 5 cm×12.5 cm strip of urethane-coated adhesive tape was laminated to a diaper polyethylene film. The adhesive portion of a 2.54 cm wide strip of test tape was partially masked to give a 2.54×2.54 cm square of adhesive that was then placed in contact with the exposed urethane-coated surface of the laminated adhesive tape strip. Using a 1000 gm roller, the tape was rolled down at the rate of 30.5 cm/min. The laminated adhesive tape strip was then gripped in a jaw, and a 1000 gm weight was connected to the free end of the partially masked tape. The time required for the partially masked tape to pull free from the laminated tape strip was measured in minutes.

135 degree peel adhesion

The polyethylene film or urethane-coated tape was adhered securely to a 5×12.5 cm steel panel. In the case of the polyethylene, a double-coated adhesive tape was placed on the steel panel before the polyethylene was attached. The 2.54 cm wide test tape strip was then placed on the film and was rolled down once in each direction at the rate of 30.5 cm/min. using a 1000 gm roller. The panel was placed in a 135 degree jig. The jig was placed into the bottom Jaw of an Instron™ 1122 while the tape was held by the upper jaw. The upper Jaw was set in motion at 30.5 cm/min. while the steel panel was moved so as to keep the tape at a 135 degree angle to the panel. The force (N/M) required to remove the tape was recorded as the peel adhesion value.

90 degree peel adhesion

A 5×15 cm strip of test tape was placed adhesive side up on a work bench. To the test tape was applied a 2.54×15 cm piece 280 micron thick polyethylene. The polyethylene was covered with a piece of silicone-treated paper and was rolled down one pass each way with a 100 gm mechanical roller at 30.5 cm/min., to form a laminate. The laminate was placed adhesive test tape down into a vacuum jig which was, in turn, placed into the lower Jaw of the Instron™ 1122. The polyethylene was then placed into the upper jaw. The vacuum, when activated, held the test tape in place. The polyethylene was peeled off at 30.5 cm/min. while maintaining it at a 90 degree angle to the tape. Peel adhesion values are reported in N/M.

180 Deg. Peel Adhesion from Polyethylene

The test procedure was similar to that described for the 135 deg. peel adhesion test, except that the steel panel was placed directly into the bottom jaw of the Inston™ 1122 test instrument. When the tape was peeled from the polyethylene, the tape was peeled at a 180 deg. angle.

Materials Used

Kraton™ 1101 was a styrene-butadiene block copolymer comprised predominately of triblock polymers with about 15 percent diblock polymer, Tg was −85° C. with approximately 31 percent styrene available from Shell Chemical Co.

Kraton™ 1118 a styrene-butadiene block copolymer comprised of about 20 percent triblock with the remaining portion being diblock, the Tg was −85° C. with about 30 percent styrene, available from Shell Chemical Co.

Solprene ™ 1205 was a styrene-butadiene tapered diblock copolymer with a Tg of −77° C. and about 25 percent styrene, available from Fina Oil and Chemical Co.

Shellflex™ 371 was a naphthenic oil, available from Shell Chemical Co. having a Tg of −64° C.

Piccolyte™ α-135 was an α-pinene resin having a Tg of 89° C. available from Hercules Chemical Co.

Zonatac™ 105 was a styrenated d-limonene resin having a Tg of 59° C. available from Arizona Chemical Co.

Zonarez ™ A-100 was an α-pinene resin having a Tg of 55° C. available from Arizona Chemical Co.

Escorez™ 2520 was a liquid aliphatic/aromatic resin having a Tg of −20° C. available from Exxon Chemical Co.

Foral™ 85 was a hydrogenated glycerol rosin ester resin having a Tg of 40° C. available from Hercules Chemical Co.

Examples 1–9

These examples (Table 1, formulations given in parts by weight) were adhesive coated from solution (toluene) to a coating weight of about 9.4 gm/square meter. All samples were then peel tested at 90 degrees from polyethylene and 135 degrees from urethane-coated tapes, see Table 2. Examples C1, C3, C5 and C7 exhibited relative low peels to polyethylene particularly after heat aging for 15 days at 49° C. The peels for invention Examples 2, 4, 6, 8 and 9 were comparatively high, and they retained a substantial proportion of their adhesion even after heat aging (H.A.). These examples demonstrate the effect of CMTg values (shown as Tg in Table 1). A CMTg of −8° C. provides generally inferior adhesive properties to polyethylene, while adhesives with similar elastomeric phases exhibit superior adhesion to polyethylene at CMTg's of −19° C. and −13° C. Example 8 shows a slight decrease in peel adhesion where the relative proportion of solid tackifier and oil-to-elastomer increased to 1.56:1. Generally, it is preferred that the ratio of tackifier phase-to-elastomer phase be less than 1.7:1.

TABLE 1

| Example | Kraton ™ 1118 | Solprene ™ 1205 | Percent Diblock | Piccolyte ™ α-135 | Shellflex ™ 371 | Tg °C. |
|---|---|---|---|---|---|---|
| C1 | 90 | 10 | 82 | 139.1 | 30.9 | −8 |
| 2 | 90 | 10 | 82 | 98.2 | 21.8 | −19 |
| C3 | 90 | 15 | 83 | 146.0 | 32.5 | −8 |
| 4 | 75 | 25 | 85 | 118.6 | 26.4 | −13 |
| C5 | 60 | 40 | 88 | 139.1 | 30.9 | −8 |
| 6 | 90 | 15 | 83 | 103.1 | 22.9 | −19 |
| C7 | 90 | 40 | 87 | 180.8 | 40.2 | −8 |
| 8 | 90 | 40 | 87 | 127.6 | 28.4 | −19 |
| 9 | 60 | 40 | 88 | 98.2 | 21.8 | −19 |

TABLE 2

| Example | 90° Peel[1] | HA | 135° Peel[2] | HA | 135° Peel[3] | HA |
|---|---|---|---|---|---|---|
| C1 | 114 | 53 | 57 | 32 | 13 | 9 |
| 2 | 468 | 85 | 404 | 293 | 47 | 31 |
| C3 | 126 | 58 | 55 | 27 | 12 | 7 |
| 4 | 489 | 366 | 220 | 113 | 26 | 18 |
| C5 | 206 | 77 | 57 | 39 | 14 | 12 |
| 6 | 464 | 378 | 414 | 256 | 44 | 27 |
| C7 | 104 | 38 | 44 | 26 | 12 | 9 |
| 8 | 359 | 282 | 318 | 253 | 198 | 170 |
| 9 | 445 | 367 | 386 | 282 | 73 | 46 |

[1]Peel was against smooth polyethylene
[2]Peel was against matte urethane release coated polypropylene film
[3]Peel was against smooth urethane release coated biaxially oriented polypropylene film

Examples 10–30

These examples were prepared substantially as were Examples 1–9. All tapes were then tested for 180 degree and 90 degree peel from a diaper polyethylene. The tapes were also shear tested against a urethane-coated biaxially oriented polypropylene. The tapes were also tested after heat aging (H.A.) for 15 days at 49° C.

Examples C11, C16, C24, C29 and C30 all had CMTg values (Tg in Table 3) of greater than −10° C. Similar to Examples C1, C3, C5 and C7, in Tables 1 and 2, these films exhibited generally low peel values to polyethylene as shown in Table 4 and low initial peels to nonwovens as shown in Table 5.

Examples 15 and C16, 20, C28 and C29 all had diblock percentages of 95 percent or higher and exhibited cohesive failure, but Examples 15 and 20 had significantly higher shear values. For Examples 15 and 20, the CMTg values were less than −10° C., and the diblock percentage was less than 98% but higher than 95%. The shear values also significantly dropped off for comparative example C25 where the CMTg value was less than −25° C. using a less preferred solid tackifier. Shear and cohesive performance were excellent when the CMTg was greater than −25° C., but less than −10° C., and the diblock percent of the elastomer phase was less than 95.

Examples 18, 19 and 20 are compositionally identical to Examples 12, 13 and 15 except the naphthionic oil was replaced with an aliphatic aromatic liquid resin with higher Tg, which adversely effected peel performance. The oil performed better even at comparable CMTg's (compare Example 14 with Example 19). Comparing Example 17 (78.8% diblock) with Examples 21, 12, 13 and 15, it can be seen that, all else being essentially equal, the adhesives with diblock percentages of 80, 85, 90 and 95 percent, respectively, had superior adhesion to polyethylene (Tables 4 and 5). Compare also Example 14 with Example 22, where an 85 percent diblock-based adhesive had better adhesion than an essentially equivalent adhesive at 80 percent diblock.

Adhesive Examples 12, 14, 18, 21, 22, C23 and C24 were also formed into tapes by hot-melt coating onto the same backing. These tapes were then peel tested, the results of which are shown as the second entries in the peel adhesion columns of Table 4. Generally, these tapes performed similarly to the solvent-coated tapes. Variations could be due to residue solvent in the solvent-coated examples or extrusion variability.

TABLE 3

| Example | Kraton™ 1118 | Solprene™ 1205 | Percent Diblock | Piccolyte™ α-135 | Shellflex™ 371 | Tg °C. |
|---|---|---|---|---|---|---|
| 10 | 50 | 50 | 90 | 120 | 25 | -12 |
| C11 | 50 | 50 | 90 | 140 | 30 | -7 |
| 12 | 50 | 50 | 90 | 101 | 20 | -17 |
| 13 | 75 | 25 | 85 | 101 | 20 | -17 |
| 14 | 75 | 25 | 85 | 120 | 25 | -12 |
| 15 | 25 | 75 | 95 | 101 | 20 | -17 |
| C16 | 25 | 75 | 95 | 140 | 20 | -4 |
| 17 | 25[1] | 75 | 78.8 | 101 | 20[2] | -17 |
| 19 | 75 | 25 | 85 | 101 | 20[2] | -12 |
| 20 | 25 | 75 | 95 | 101 | 20[2] | -11 |
| 21 | 100 | 0 | 80 | 100 | 20 | -18 |
| 22 | 100 | 0 | 80 | 120 | 25 | -12 |
| 23 | 100 | 0 | 80 | 100 | 20[2] | -12 |
| C24 | 100 | 0 | 80 | 120 | ·20[2] | -5 |
| C25 | 75 | 25 | 85 | 120[3] | 20 | -26 |
| 26 | 75 | 25 | 85 | 120[4] | 25 | -21 |
| 27 | 75 | 25 | 85 | 120[5] | 20 | -21 |
| C28 | 0 | 100 | 100 | 120 | 20 | -10 |
| C29 | 0 | 100 | 100 | 120 | 20[2] | -5 |
| C30 | 50 | 50 | 90 | 120 | 20[2] | -5 |

[1] Kraton™ 1101 was used instead of Kraton™ 1118
[2] Escorez™ 2520 was used instead of Shellflex™ 371
[3] Foral™ 85 was substituted for Piccolyte™ α135
[4] Zonatac™ 105 das substituted for Piccolyte™ α135
[5] Zonarez™ A-100 was substituted for Piccolyte™ α135

TABLE 4

| Example | 180° Peel Polyethylene | HA | 90° Peel Polyethylene | HA | SHEAR | HA |
|---|---|---|---|---|---|---|
| 10 | 1100 | 608 | 388 | 192 | 5600+ | 8500+ |
| C11 | 688 | 309 | 73 | 18 | 5600+ | 8500+ |
| 12 | 1115/970 | 647/966 | 419/586 | 234/274 | 5600+ | 8500+ |
| 13 | 995 | 763 | 607 | 402 | 5600+ | 8500+ |
| 14 | 1043/956 | 797/657 | 566/452 | 296/93 | 5600+ | 8500+ |
| 15 | 840 | 850 | 523 | 365 | 1043 | 855c |
| C16 | 429 | 435 | 31 | 48 | 604 | 774c |
| 17 | 643 | 522 | 296 | 206 | 5600+ | 8500+ |
| 18 | 672/797 | 637/797 | 172/348 | 200/190 | 5600+ | 8500+ |
| 19 | 622 | 576 | 122 | 136 | 5600+ | 8500+ |
| 20 | 715 | 603 | 124 | 184 | 774 | 1552c |
| 21 | 838/941 | 575/753 | 479/560 | 251/364 | 4000+ | 5700+ |
| 22 | 937/903 | 314/797 | 415/317 | 58/314 | 4000+ | 5700+ |
| 23 | 792/807 | 319/246 | 222/178 | 97/127 | 4000+ | 5700+ |
| C24 | 241/422 | 140/290 | 33/26 | 17/17 | 4000+ | 5700+ |
| C25 | 802 | 541 | 354 | 274 | 183 | 150 |
| 26 | 792 | 618 | 464 | 355 | 574 | 1405 |
| 27 | 995 | 666 | 514 | 350 | 3434 | 5700+ |
| C28 | 894 | 527 | 176 | 144 | 26 | 36c |
| C29 | 493 | 391 | 48 | 54 | 31 | 32c |
| C30 | 239 | 150 | 21 | 10 | 5400+ | 4000+ |

TABLE 5

| | 135° Peel Nonwoven | | 180° Peel |
|---|---|---|---|
| Example | Initial | 24 hours | Polyethylene (3 mth age) |
| 10 | 342 | 371 | 700 |
| C11 | 90 | 250 | 333 |
| 12 | 329 | 313 | 1033 |
| 13 | 348 | 359 | 884 |
| 14 | 348 | 388 | 879 |
| 15 | 253 | 252 | 971 |
| C16 | 80 | 254 | 338 |
| 17 | 244 | 358 | 546 |
| 18 | 228 | 335 | 594 |
| 19 | 154 | 301 | 604 |
| 20 | 230 | 302 | 599 |

Example 31

An adhesive was solvent coated onto a standard backing at 7.1 grains (gms/24 in²) (29.8 gm/100 cm²). The composition comprised 75 parts Kraton™ 1118, 25 parts Solprene™ 1205, and 145 parts Piccolyte™ α-135 to yield an adhesive with a CMTg of 5° C. and 85 parts diblock by weight, the adhesive was tested for 135 degree peel against the same diaper polyethylene as in Examples 1–9 to yield an average peel of 3.4 gms/in (1.3 N/m). The average 135 degree peel from a diaper nonwoven was 4.8 gm/in (1.8 N/m). This adhesive is nonfunctional.

Example 32

An adhesive was solvent coated onto a standard backing at 7.25 gms/24 in$^2$ (30.4 gm/100 cm$^2$). The composition comprised 70 parts Kraton™1118, 10 parts Solprene™ 1205, and 120 parts Piccolyte™ α-135 to yield an adhesive with a CMTg of –3° C. and a diblock content of 82 parts by weight. The adhesive was tested as outlined in Example 31 above giving an average 135 degree peel to polyethylene of 59.6 gm/in (23 N/m) and an average 135 degree peel to nonwovens of 13.9 gms/in (5.4 N/m). This adhesive has insufficient peel adhesion to adequately function as a permanent adhesive to nonwovens or polyethylene.

The various modifications and alterations of this invention will be apparent to those skilled in the art without departing from the scope and spirit of this invention, and this invention should not be restricted to that set forth herein for illustrative purposes.

I claim:

1. A pressure-sensitive adhesive tape comprising a backing and a hot melt coatable pressure-sensitive adhesive layer, the adhesive layer comprising 100 parts of an elastomeric phase and a tackifying phase, the adhesive having a CMTg value of less than about –10° C., the elastomeric phase comprised of from about 78 to 98 parts of a diblock A–B type block copolymer portion, of which the B block is comprised predominately of 1,3-butadiene and the A block is comprised predominately of monoalkenyl arene, and about 2 to 22 parts of a multiblock elastomer portion of the elastomeric phase comprising an A–B type block copolymer of at least 3 blocks, the B block comprised predominately of 1,3-butadiene and the A block comprised of monoalkyl arene, the tackifying phase, per 100 parts of the elastomeric phase, comprised of about 80 to 140 parts of a solid tackifying resin and 5 to 35 parts of a liquid tackifier.

2. The adhesive tape of claim 1 wherein the adhesive CMTg value is from –25° C. to –10° C., the diblock copolymer portion comprises 80 to 95 parts of the elastomeric phase and the multiblock A–B type block copolymer elastomer portion comprises 20 to 5 parts of the elastomeric phase.

3. The adhesive tape of claim 2 wherein the solid tackifying resin is a hydrocarbon resin or aliphatic/aromatic hydrocarbon resin at from about 80 to 135 parts.

4. The adhesive tape of claim 3 wherein the liquid tackifier is a liquid tackifying resin.

5. The adhesive tape of claim 3 wherein the liquid tackifier is a plasticizing oil at from about 5 to 30 parts.

6. The adhesive tape of claim 3 wherein the multiblock A–B type block copolymer elastomer portion is a triblock copolymer.

7. The adhesive tape of claim 2 wherein the multiblock A–B type block copolymer elastomer portion is a linear triblock copolymer and the solid tackifying resin comprises poly-alpha-pinene, a rosin ester or a hydrogenated rosin ester.

8. A hot-melt coatable pressure-sensitive adhesive comprising 100 parts of an elastomeric phase and a tackifying phase, the adhesive having a CMTg value of less than about –10° C., the elastomeric phase comprised of from 78 to 98 parts of a diblock A–B type block copolymer portion, of which the B block is comprised predominately of 1,3-butadiene and the A block is comprised predominately of monoalkenyl arene, and 2 to 22 parts of a multiblock elastomer portion of the elastomeric phase comprising an A–B type block copolymer of at least 3 blocks, the B block comprised predominately of 1,3-butadiene and the A block comprised of monoalkyl arene, the tackifying phase, per 100 parts of the elastomeric phase, comprised of about 80 to 140 parts of a solid tackifying resin and 5 to 35 parts of a liquid tackifier.

9. The adhesive of claim 8 wherein the adhesive CMTg value is from –25° C. to –10° C., the diblock copolymer comprises 80 to 95 parts of the elastomeric phase and the multiblock A–B type block copolymer comprises 20 to 5 parts of the elastomeric phase.

10. The adhesive of claim 9 wherein the solid tackifying resin is a hydrocarbon resin or an aliphatic/aromatic hydrocarbon-resin at from about 80 to 135 parts.

11. The adhesive of claim 10 wherein the liquid tackifier is a liquid tackifying resin.

12. The adhesive of claim 10 wherein the liquid tackifier is a plasticizing oil at from about 5 to 30 parts.

13. The adhesive of claim 10 wherein the multiblock A–B type block copolymer is a linear triblock copolymer.

14. The adhesive of claim 12 wherein the solid hydrocarbon resin has a softening point of from 80° C. to 135° C. and comprises poly-alpha-pinene, a rosin ester or a hydrogenated rosin ester.

15. The adhesive of claim 12 wherein the hydrocarbon resin is formed predominately of α-pinene species.

16. The adhesive of claim 12 wherein the multiblock A–B type block copolymer is a linear triblock copolymer.

* * * * *

UNITED STATES PATENT AND TRADEMARK OFFICE
CERTIFICATE OF CORRECTION

PATENT NO. : 5,453,319

DATED : September 26, 1995

INVENTOR(S) : Ramsis Gobran

It is certified that error appears in the above-indentified patent and that said Letters Patent is hereby corrected as shown below:

Col. 1, line 57, "cariflex TM" should read --Cariflex TM--.

Col. 3, line 16, "dienee" should read --dienes--.

Col. 5, line 20, this sentence should be a paragraph heading.

Col. 5, line 44, "Jaw" should read --jaw--.

Col. 5, line 45, "Jaw" should read --jaw--.

Col. 6, line 10, "Jaw" should read --jaw--.

Col. 6, line 12, "Jaw" should read --jaw--.

Col. 6, line 21, "piece 280" should read --piece of 280--.

Col. 6, line 26, "Jaw" should read --jaw--.

Col. 7, Table 2, under "Example 2, HA", "85" should read --385--.

Col. 8, line 41, "14" should not be in bold characters.

Col. 9, Table 3, the heading "Percent Diblock" should read --Diblock Percent--.

Col. 9, Table 3, Example 18 has been left out. Insert line 18 between lines 17 and 19 as follows:
--18, 50, 50, 90, 101, $20^2$, -11--.

Col. 9, Table 3, under "Example 17, Shellflex TM 371", "$20^2$" should read --20--.

Col. 9, Table 3, after Table 3 "105 das substituted" should read --105 was substituted--.

Col. 9, Table 4, under "Example 22, 180° Peel Polyethylene", "937/903" should read --937/908--.

UNITED STATES PATENT AND TRADEMARK OFFICE
CERTIFICATE OF CORRECTION

PATENT NO. : 5,453,319

DATED : September 26, 1995

INVENTOR(S) : Ramsis Gobran

It is certified that error appears in the above-indentified patent and that said Letters Patent is hereby corrected as shown below:

Col. 9, Table 4, under "Example C30, 180° Peel Polyethylene", "239" should read —237—.

Signed and Sealed this

Thirtieth Day of July, 1996

Attest:

BRUCE LEHMAN

Attesting Officer

Commissioner of Patents and Trademarks